PROTEIN FOR INHIBITING COLLAGEN-STIMULATED PLATELET AGGREGATION

United States Patent [19]

Connolly et al.

[11] Patent Number: 5,340,726
[45] Date of Patent: Aug. 23, 1994

[54] PROTEIN FOR INHIBITING COLLAGEN-STIMULATED PLATELET AGGREGATION

[75] Inventors: Thomas M. Connolly, Harleysville; Paul M. Keller, Lansdale; Lloyd H. Waxman, Ottsville, all of Pa.

[73] Assignee: Merck & Co., Inc., Rahway, N.J.

[21] Appl. No.: 107,411

[22] Filed: Aug. 16, 1993

Related U.S. Application Data

[63] Continuation of Ser. No. 844,303, Feb. 27, 1992, abandoned.

[51] Int. Cl.$^5$ .................... C12N 5/00; C07K 3/00; C12P 21/06; C07H 15/12
[52] U.S. Cl. ................... 530/350; 435/174; 435/320.1; 435/240.2; 435/254.21; 435/69.1; 530/355; 530/422
[58] Field of Search ............ 435/240.2, 255, 256, 435/69.1, 320.1; 530/350, 351, 355, 356; 536/23.1

[56] References Cited

PUBLICATIONS

J. Mol. Biol. (1986) 189, 113–130 Studier et al., Use of Bacteriophage T7RNA Polymerase to Direct Selective Highlevel Expression of Cloned Genes.
Gene, 56 (1987) 125–135 Elsevier, Rosenberg et al., Vectors for selective expression of cloned DNAs by T7 RNA polymerase.
The Journal of Cell Biology, vol. 99 (1984) 2048–2055, Shadle et al., Platelet–Collagen Adhesion: Evidence for Participation of Antigenically Distinct Entities.
The Journal of Cell Biology, vol. 99, (1984) 2056–2060, Shadle et al., Platelet–Collagen Adhesion: Inhibition by a Monoclonal Antibody That Binds Glycoprotein IIb.
Thrombosis Research, vol. 12, No. 5, pp. 841–850, Fauvel et al., Platelet–Collagen Interaction: Adhesion of Human Blood Platelets to Purified (CB4) Peptide from Type III Collagen.
Platelet Adhesion to Collagen, vol. 94, No. 3, Legrand et al., Specific and Quantitative method for estimation of platelet adhesion to fibrillar collagen*.
Thrombosis Research 17; 285–287 (1980), Fauvel et al., Letter to the Editor in Chief.
Kanczewski et al. (Dec. 8–12, 1991) J Cell Biol 115 (3 part 2), 442 A.
Waxman et al. (1990) Science V. 248. pp. 593–596.

Primary Examiner—Robert J. Hill, Jr.
Assistant Examiner—Gian P. Wang
Attorney, Agent, or Firm—Richard S. Parr; Melvin Winokur; Paul D. Matukaitis

[57] ABSTRACT

A protein which inhibits collagen-stimulated platelet aggregation. The protein has a molecular weight of approximately 17,000. A method of isolating the protein from *Ornithodoros moubata* and using the protein to prevent or delay blood coagulation by blocking the stimulation of platelet aggregation by collagen is also described. The protein is useful in the prevention, prophylaxis, therapy and treatment of thrombotic diseases.

2 Claims, 1 Drawing Sheet

FIG. 1

PROTEIN FOR INHIBITING COLLAGEN-STIMULATED PLATELET AGGREGATION

This is a continuation of application Ser. No. 07/844,303 filed on Feb. 27, 1992, now abandoned.

BACKGROUND OF THE INVENTION

Normal hemostasis in man is governed by a complex series of interrelated mechanisms involving both cellular and humoral biochemical components. The biochemical pathway involves injury to intact endothelial cells, stimulation of platelets and activation of coagulation mechanisms. When a vessel is damaged and the subendothelium is exposed, platelets very rapidly adhere to some of the constituents of the vessel wall, notably collagen. Although platelets also adhere to other subendothelial constituents, only collagen has been reported to stimulate platelets to release their granule contents and recruit other platelets to the injury site.

SUMMARY OF THE INVENTION

The invention comprises a protein (Moubatin) isolated from *Ornithodoros moubata* tick extract which blocks collagen-stimulated platelet aggregation. The protein has a molecular weight of approximately 17,000. The invention also comprises methods of preparing the protein, such as by purifying the protein from *Ornithodoros moubata* extract, and a method of using the protein to prevent or delay blood coagulation by blocking collagen-stimulated platelet aggregation. The protein is useful in the prevention, prophylaxis, therapy and treatment of thrombotic diseases.

DETAILED DESCRIPTION OF THE INVENTION

The invention encompasses the preferred protein isolated from *Ornithodoros moubata* or expressed in transformed *Saccharomyces cerevisiae*, and homologs, isoforms or genetic variants, provided that each one blocks collagen-stimulated platelet aggregation and reacts with antibodies specific for the specified protein.

Proteins

The invention includes Moubatin, variations on the disclosed purified protein sequence which conserve the activity of the disclosed sequence, including fragments or subunits, naturally occurring mutations, allelic variants, randomly generated artificial mutants and intentional sequence variations which conserve activity. Fragments or subunits refers to any portion of the sequence which contains fewer amino acids than the complete protein, e.g. partial sequences excluding portions at the N- and/or C-termini of the complete protein.

Proteins of the invention also include disclosed recombinant protein sequences which conserve the activity of the purified protein sequences. Also included are hybrid proteins, such as fusion proteins or proteins resulting from the expression of multiple genes within the expression vector, and may include a polypeptide having the specific activity of a disclosed protein linked by peptide bonds to a second polypeptide.

It will be understood that other variants of the proteins of the present invention are included, especially any variants that differ from the isolated protein only by conservative amino acid substitution. Such conservative amino acid substitutions are defined as "sets" in Table I of Taylor, *J. Mol. Biol.*, 188, 233 (1986).

Moubatin is the preferred protein of the invention. Preferably, the protein is obtained by expression in transformed Saccharomyces cerevisiae as described below.

Identification of Inhibition of Collagen-Stimulated Platelet Aggregation

Blood was anticoagulated with acid citrate dextrose, and the human platelets were washed and isolated in modified Tyrode's buffer with no $Ca^{++}$, pH 6.5. The final platelet suspension was in a modified Tyrode's buffer without $Ca^{++}$ (134 mM NaCl, 3 mM $NaH_2PO_4$, 2 mM $MgCl_2$, 5 mM glucose, 12 mM $NaHCO_3$, 3.5 mg/ml bovine serum albumin at pH 7.4) adjusted to $3 \times 10^8$ platelets/ml after counting in a model ZM Coulter Counter (Hialeah, Fla.). Aggregation of the washed platelets was used to monitor platelet inhibitory activity in the tick soluble extracts and for each of the fractions tested throughout the purification of Moubatin. The tick extract, column fraction, or aliquot of purified protein was incubated with 0.2 or 0.25 ml platelets at 37° C. with 0.2 mg/ml human fibrinogen. Collagen at 1 or 2 $\mu g/ml$, or another agonist, was added and the aggregation was monitored in a Sienco or a Chronolog aggregometer. The percentage inhibition was calculated based on the final extent of aggregation of the test samples compared to the appropriate buffer control. Inhibitory activity is defined as a decrease in the rate and/or extent of platelet aggregation.

Identification of Blocking of Platelet Adhesion to Collagen

Recombinant, yeast-expressed Moubatin does not inhibit the adhesion of washed platelets to Collagen-coated microtiter plates.

Polystyrene 96-well microtiter plates (Costar, Cambridge, Mass.) are coated with 100 $\mu l$ per well of 40 $\mu g/ml$ collagen dissolved in 5 mM acetic acid for 1 hour at room temperature followed by blocking of the nonspecific cell binding sites by addition of 200 $\mu l$ of 10 mg/ml heat-denatured BSA for 1 hour. Control wells are coated with BSA only. The wells are rinsed three times with HEPES buffered saline (HBS) containing 20 mM HEPES, pH 7.4, 0.14 M NaCl, and 2 mM $MgCl_2$. 100 $\mu l$ of washed platelets are incubated with various concentrations of Moubatin or buffer as a control for 5 min at room temperature and then added to each collagen coated well and incubated at room temperature for 45 min., nonadherent platelets are removed by aspiration, and the wells are rinsed three times with 200 $\mu l$ of HBS. The number of adhered platelets is determined by protein assay, using the BCA reagent and measuring the absorbance of each well at 562 nM.

EXAMPLE 1

Isolation of Collagen-stimulated Platelet Aggregation Inhibitor From *Ornithodoros moubata* Extract

Purification

*Ornithodoros moubata* ticks were obtained frozen from Antibody Associates, Ltd. (Bedford, Tex.) and stored at −70° C. until used. A typical preparation was initiated with 400–500 whole ticks constituting about 12 grams of material. The ticks were disrupted in batches of 50 with a Polytron (Brinkmann Inst. Co., Westbury, N.Y.) in 10 ml of 25 mM Hepes buffer, pH 7.0, containing 0.15 M NaCl and the protease inhibitors E-64, pepstatin, chymostatin, and leupeptin (50 uM each). The homogenate was centrifuged at 100,000×g for 20 min and the resulting pellets were reextracted in 5 ml of the same buffer and recentrifuged. The combined supernatants (approx. 800 mg protein) were tested for inhibitory activity. Extracts were prepared similarly for the purification of Moubatin.

The crude soluble extract was diluted 3-fold with water to lower the ionic strength and applied to a 25 ml Fast Q Column equilibrated in 25 mM Bis-Tris (pH 7.0). The column was washed with the same buffer until the absorbance at 280 nm decreased to less than 0.05. The bound proteins were eluted with 0.8 M NaCl (100 ml) in the same buffer, dialyzed against water to removed the salt, and lyophilized in the presence of 0.1 mg/ml sucrose. The lyophilized material was applied to a column of Sephadex G-50 Superfine (2.5×50 cm) equilibrated in 50 mM Hepes (pH 7.0).

The fractions that contained platelet aggregation inhibitory activity, which eluted in one peak, were pooled and applied to an anion exchange column (Pharmacia Mono Q, 1×10 cm) equilibrated in 20 mM Bis-Tris (pH 6.0) controlled by an FPLC system. The bound proteins were eluted with a gradient of NaCl (0 to 0.3 M) in the same buffer. Two peaks of inhibitory activity (designated AP-1 and AP-2) were found which eluted at approximately 0.12 and 0.25 M NaCl. The active fractions in each were pooled and concentrated by lyophilization. The dried material was redissolved in 1.5 ml H$_2$O and applied to a column (1.5×50 cm) of Sephadex G-75 Superfine equilibrated in 50 mM Hepes (pH 7.0). On gel filtration both AP-1 and AP-2 eluted in one peak with an M$_r$ ~15–20 kDa.

The final purification step consisted of fractionation of the pooled activity after gel filtration on repeated reverse phase HPLC on a Pro RPC column (0.5×10 cm)(Pharmacia) controlled by an FPLC system. The column was equilibrated in 0.1% (v,v) trifluoroacetic acid in water and the bound proteins were eluted with a gradient of acetonitrile (0 to 50%) also in 0.1% trifluoroacetic acid. 0.5 ml fractions were collected and the solvents were removed by centrifugation under vacuum in a Speed Vac. Fractions were reconstituted with ~100 μl 20 mM Hepes (pH 7.0) before assay and analysis by SDS-PAGE.

Moubatin has a molecular weight of 17,256, which is deduced from the predicted amino acid sequence, and the following amino acid composition:

| Amino Acid | Residues/mole |
| --- | --- |
| Ala | 10 |
| Arg | 4 |
| Asn | 6 |
| Asp | 15 |
| Cys | 6 |
| Gln | 9 |
| Glu | 7 |
| Gly | 13 |
| His | 2 |
| Ile | 5 |
| Leu | 12 |
| Lys | 16 |
| Met | 2 |
| Phe | 4 |

-continued

| Amino Acid | Residues/mole |
| --- | --- |
| Pro | 5 |
| Ser | 13 |
| Thr | 12 |
| Trp | 3 |
| Tyr | 5 |
| Val | 7 |

EXAMPLE 2

In vitro Activity of the Moubatin

Our studies show that while platelet aggregation is stimulated by 2 μg/ml collagen, addition of the collagen-stimulated platelet aggregation inhibitor isolated in Example 1 inhibits such stimulation. The IC$_{50}$ for this inhibition was 50 nM.

Moubatin is a specific inhibitor of collagen-induced platelet aggregation. At a concentration that blocks platelet aggregation induced by collagen, moubatin does not inhibit aggregation initiated by other agonists of platelets including thrombin, ADP, arachidonic acid, ristocetin, and A23187. Moubatin also inhibits collagen-induced intracellular Ca$^{++}$ mobilization. Unlike other known inhibitors (e.g. LAPP as described in *Journal of Biological Sciences* Vol. 267 (1992) (in press)) of collagen stimulation of platelets, moubatin does not block platelet adhesion to collagen in adhesion assays.

Recombinant DNA Technology

Recombinant DNA technology may be used to produce proteins of the invention, preferably Moubatin. This technology allows segments of genetic information, DNA, from different cells, and usually from different organisms, to be joined end-to-end outside the organisms from which the DNA was obtained and to incorporate this hybrid DNA into a cell that will allow the production of the protein for which the original DNA encodes. Genetic information, DNA or mRNA, is isolated and incorporated into an appropriate cloning vector, and transduced into an appropriate host cell.

Cloning vectors useful for this technology include a DNA sequence which accommodates specific experimental foreign DNA. The vectors are introduced into host cells that can exist in a stable manner and express the protein dictated by the experimental DNA. Cloning vectors may include plasmids, bacteriophage, viruses and cosmids.

Expression vectors are DNA sequences that are required for the transcription of cloned copies of genes and the translation of their mRNAs in an appropriate host. These vectors can express either procaryotic or eucaryotic genes in a variety of cells such as bacteria, yeast, insect and mammalian cells. Proteins may also be expressed in a number of virus systems. A suitably constructed expression vector contains an origin of replication for autonomous replication in host cells, selective markers, a limited number of useful restriction enzyme sites, a high copy number, and strong promoters. Promoters are DNA sequences that direct RNA polymerase to bind to DNA and initiate RNA synthesis; strong promoters cause such initiation at high frequency. Expression vectors may include, but are not limited to cloning vectors, modified cloning vectors and specifically designed plasmids or viruses.

Expression Systems

The preferred expression system for preparing recombinant Moubatin is described in Example 3. The system uses yeast strain *Saccharomyces cerevisiae* BJ1995.

Expression systems useful in the eucaryotic systems of the invention comprise promoters derived from appropriate eucaryotic genes. A class of promoters useful in yeast, for example, include promoters for synthesis of glycolytic enzymes, including those for 3-phosphoglycerate kinase (Hitzeman et al., *J. Biol. Chem.* (1980) 255:2073). Other promoters include those from the enolase gene (Holland, M. J., et al., *J. Biol. Chem.* (1981) 256:1385) or the Leu2 gene obtained from YEp13 (Broach, J., et al., *Gene* (1978) 8:121).

Vector Construction

Figure 1:
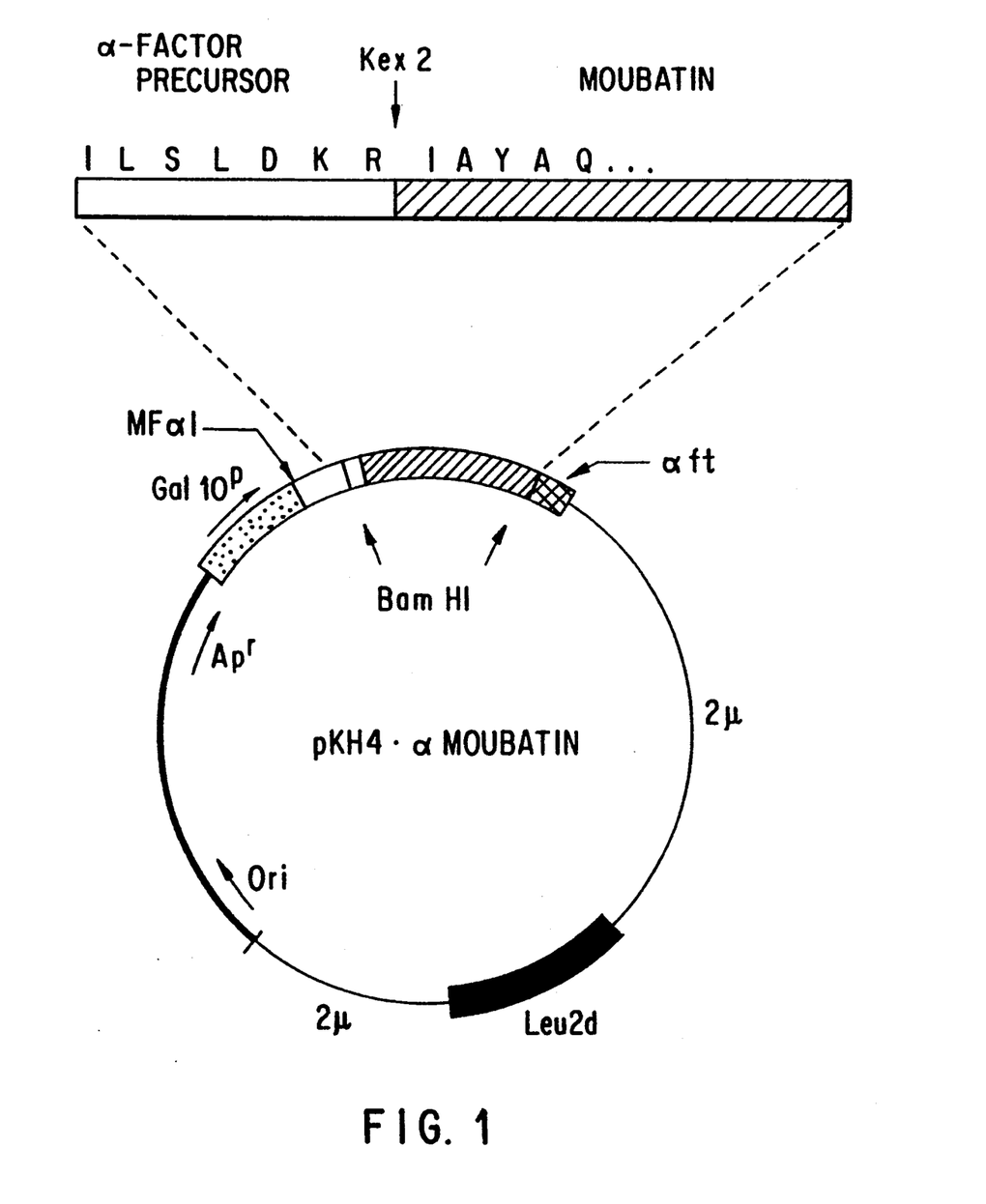
FIG. 1 shows the yeast vector used for expression of the Moubatin synthetic gene sequence.

The expression vector preferred for preparing recombinant Moubatin in yeast, is described in Example 3 and FIG. 1.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g. New England Biolabs, Product Catalog. In general, about 1 $\mu$g of plasmid or DNA sequence is cleaved by one unit of enzyme in about 20 $\mu$l of buffer solution. Typically, an excess of restriction enzyme is used to ensure complete digestion of the DNA substrate. Incubation times of about 1 to 2 hours at about 37° C. are workable, although variations can be tolerated. After each incubation, the digestion product is exposed to phenol/chloroform extraction and may be followed by running over a Sephadex ® G-50 spin column. If desired, size separation of the cleaved fragments may be performed by polyacrylamide gel or agarose gel electrophoresis using standard techniques. A general description of size separations is found in *Methods in Enzymology* (1980)65: 499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° to 25° C. in 50 mM Tris, pH 7.6, 50 mM NaCl, 6 mM MgCl$_2$, 6 mM DTT and 5–10 $\mu$MdNTPs. The Klenow fragment fills in 5' overhangs but removes protruding 3' single strands, even in the presence of the four dNTPs. If desired, selective repair can be performed by supplying selected dNTPs within the limitations dictated by the nature of the sticky ends. After treatment with Klenow, the mixture is extracted with phenol/chloroform and ethanol precipitated followed by running over a Sephadex ® G-50 spin column. Treatment under appropriate conditions with S1 nuclease results in hydrolysis of any single-stranded portion.

As mentioned above, oligonucleotides may be prepared by the triester method of Matteucci, et al. (*J. Am. Chem. Soc.* (1981) 103:3185) or using commercially available automated oligonucleotide synthesizers.

Kinasing of single strands prior to annealing or for labelling is achieved using an excess, e.g., approximately 10 units of polynucleotide kinase to 0.1 nmole substrate in the presence of 50 mM Tris, pH 7.6, 10 mM MgCl$_2$, 5 mM dithiothreitol, 1–2 mM ATP, 1.7 pmoles $^{32}$P-ATP(2.9 mCi/mmole), 0.1 mM spermidine, 0.1 mM EDTA.

Ligations are performed in 15–30 $\mu$l volumes under the following standard conditions and temperatures: 20 mM Tris-HCl, pH 7.5, 10 mM MgCl$_2$, 10 mM DTT, 33 $\mu$g/ml BSA, 10 mM-50 mM NACl, and 1 mM ATP, 0.3–0.6 (Weiss) units T4 DNA ligase at 14° C. (for "blunt end" ligation). Intermolecular "sticky end" ligations are usually performed at 33–100 $\mu$g/ml total DNA concentrations (5–100 nM total end concentration). Intermolecular blunt end ligations (usually employing a 10–30 fold molar excess of linkers) are performed at 1 $\mu$M total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{2+}$ using about 1 unit of BAP per $\mu$g of vector at 60° C. for about 1 hour. In order to recover the nucleic acid fragments, the preparation is extracted with phenol/chloroform and ethanol precipitated and desalted by application to a Sephadex ® G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded plasmid or phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Probing cDNA Libraries cDNA or genomic libraries are screened using the colony or plaque hybridization procedure. Each plate containing bacterial colonies (or recombinant phage-infected bacteria) is replicated onto duplicate nitrocellulose filter papers (S & S type BA-85) and, for bacterial colony screens, the colonies are allowed to grow at 37° C. for 14–16 hours on L agar containing 50 $\mu$g/ml Amp. The bacteria are lysed, plasmid or phage and DNA fixed to the filter by sequential treatment for 5 minutes each with 0.2N NaOH, 1.5M NaCl, then 0.5 M Tris pH 7.5, 1.5M NaCl and then 2×standard saline citrate (2×SSC). Filters are air dried and baked at 80° C. for 2 hours. The duplicate filters are prehybridized at 42° C. for 6–8 hours with 10 ml per filter of DNA hybridization buffer (5×SSC, pH 7.0, 5×Denhardt's solution (polyvinyl pyrrolidine, plus Ficoll and bovine serum albumin; 1×=0.02% of each), 50 mM sodium phosphate buffer at pH 7.0, 0.2% SDS, 20 μg/ml polyU, and 50 μg/ml denatured salmon sperm DNA.

The samples are hybridized with kinased probe under conditions which depend on the stringency desired. Typical moderately stringent conditions employ a temperature of 42° C. for 24–36 hours with 1–5 ml/filter of DNA hybridization buffer containing probe. For higher stringencies, high temperatures and shorter times are employed. The filters are washed four times for 30 minutes each time at 37° C. with 2×SSC, 0.2% SDS and 50 mM sodium phosphate buffer at pH 7, then are washed twice with 2×SSC and 0.2% SDS, air dried and are autoradiographed at −70° C. for 2 to 3 days.

Oligonucleotide Primers

Oligonucleotide primers are prepared which will hybridize to different strands of the desired sequence and at relative positions along the sequence such that an extension product synthesized from one primer, when it is separated from its template (complement), can serve as a template for extension of the other primer into a nucleic acid of defined length. The primers may be prepared using any suitable method, such as, for example, the phosphotriester and phosphodiester methods, described respectively in Narang, S. A., et al. *Meth. Enzymol.*, 68, 90 (1979) and Brown, E. L. et al., *Meth. Enzymol*, 68, 109 (1979), or automated embodiments thereof. In one such automated embodiment, diethylphosphoramidites are used as starting materials and may be synthesized as described by Beaucage et al., *Tetrahedron Letters* (1981), 22: 1859–1862. One method for synthesizing oligonucleotides on a modified solid support is described in U.S. Pat. No. 4,458,066. It is also possible to use a primer which has been isolated from a biological source (such as a restriction endonuclease digest).

Polymerase Chain Reaction Amplification

Large amounts of DNA coding for the protein may be obtained using polymerase chain reaction (PCR) amplification techniques as described in Mullis et al., U.S. Pat. No. 4,800,159. The extension product of one primer, when hybridized to another primer, becomes a template for the production of the nucleic acid sequence.

The primer template complexes act as substrate for DNA polymerase which, in performing its replication function, extends the primers. The region in common with both primer extensions, upon denaturation, serves as template for a repeated primer extension.

Taq DNA Polymerase catalyzes primer extension in the amplification process. The enzyme is a thermostable DNA polymerase isolated from *Thermus aquaticus*. Because it stays active through repeated elevations to high denaturation temperatures, it needs to be added only once. Deoxynucleotide triphosphates provide the building blocks for primer extension.

The nucleic acid sequence strands are heated until they separate, in the presence of oligonucleotide primers that bind to their complementary strand at a particular site of the template. This process is continued with a series of heating and cooling cycles, heating to separate strands, and cooling to reanneal and extend the sequences. More and more copies of the strands are generated as the cycle is repeated. Through amplification, the coding domain and any additional primer-encoded information such as restriction sites or translation signals (signal sequences, start codons and/or stop codons) is obtained. PCR protocols are often performed at the 100 μL scale in 0.5-mL microcentrifuge tubes. The PCR sample may be single- or double-stranded DNA or RNA. If the starting material is RNA, reverse transcriptase is used to prepare first strand cDNA prior to PCR. Typically, nanogram amounts of cloned template, up to microgram amounts of genomic DNA, or 20,000 target copies are chosen to start optimization trials.

PCR primers are oligonucleotides, typically 15 to 30 bases long, and are complementary to sequences defining the 5' ends of the complementary template strands. Non-template complementary 5' extensions may be added to primers to allow a variety of useful post amplification operations on the PCR product without significant perturbation of the amplification itself. It is important that the two PCR primers not contain more than two bases complementary with each other, especially at their 3' ends. Internal secondary structure should be avoided in primers.

Because Taq DNA Polymerase has activity in the 37°–55° C. range, primer extension will occur during the annealing step and the hybrid will be stabilized. The concentrations of the primers are preferably equal in conventional PCR and, typically, within 0.1-to 1-μM range.

In the standard PCR protocol, each deoxynucleotide triphosphate concentration is preferably about 200 μM. The four dNTP concentrations are preferably above the estimated km of each dNTP (10–15 μM).

Preferably, PCR buffer is composed of about 500 mM potassium chloride, 100 mM Tris-HCl (pH 8.3 at room temperature), 15 mM magnesium chloride, and 0.01% w/v gelatin. In the presence of 0.8 mM total dNTP concentration, a titration series in small increments over the 1.5-to 4-mM range will locate the magnesium concentration producing the highest yield of a specific product. Too little free magnesium will result in no PCR product and too much free magnesium may produce a variety of unwanted products.

Preferably, in a 100-μL reaction volume, 2.0 to 2.5 units of Taq DNA Polymerase are recommended. The enzyme can be added conveniently to a fresh master mix prepared for a number of reactions, thereby avoiding accuracy problems associated with adding individual 0.5-μL enzyme aliquots to each tube. A typical PCR protocol for amplification of the DNA template includes a 1 minute 94° C. denaturation step, a 1 minute 37° C. primer annealing step, and a 2 minute 72° C. primer extension step. This will amplify a 500 base-pair product at least 100,000-fold in 25 cycles.

During DNA denaturation, sufficient time must be allowed for thermal equilibration of the sample. The practical range of effective denaturation temperatures for most samples is 92°–95° C., with 94° C. being the standard choice.

Primer annealing is usually performed first at 37° C., and the specificity of the product is evaluated. If unwanted bands are observed, the annealing temperature should be raised in subsequent optimization runs. While the primer annealing temperature range is often 37°–55° C., it may be raised as high as the extension temperature in some cases. Merging of the primer annealing and primer extension steps results in a two-step PCR process.

Primer extension, in most applications, occurs effectively at a temperature of 72° C. and seldom needs optimization. In the two-temperature PCR process the temperature range may be 65°–70° C. In situations where enzyme concentration limits amplification in late cycles, the extension is preferably increased linearly with cyclic number. Usually, 25 to 45 cycles are required for extensive amplification (i.e., 1,000,000 fold) of a specific target.

Transformation

Depending on the host cell used, transformation is done using standard techniques appropriate to such cells. The calcium treatment employing calcium chloride, as described by Cohen, S. N., *Proc. Natl. Acad. Sci. USA* (1972) 69:2110, or the RbCl method described in Maniatis et al., *Molecular Cloning: A Laboratory Manual* (1982) Cold Spring Harbor Press, p.254 is used for procaryotes or other cells which contain substantial cell wall barriers. Infection with *Agrobacterium tumefaciens* (Shaw, C. H., et al., *Gene* (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al., *J. Bacter.* (1977) 130:946 and Hsiao, C. L. et al., *Proc. Natl. Acad. Sci. USA* (1979) 76:3829.

Example 3 describes a preferred yeast expression system for preparing recombinant Moubatin.

EXAMPLE 3

Identification of Nucleic Acid Sequence (SEQUENCE ID NO. 1) and Entire Amino Acid Sequence and Expression of 156 Amino Acid Moubatin (SEQUENCE ID NO. 2)

Identification of Nucleic Acid Sequence

A lambda ZAP II (Stratagene) tick cDNA library was constructed following the manufacturer's instructions using total tick poly (A)+RNA.

Total phage DNA from this was isolated using standard DNA isolation procedures. Using standard PCR protocols, the DNA was screened for the presence of moubatin sequences by PCR amplification. PCR analysis was run using primer pairs consisting of a λ arm primer; (primer λ 1:5'-GCTCT AGA ACT AGT GGA TCC-3') (Sequence ID No. 5), and degenerate oligonucleotide primers whose sequences were based on two Lys-C peptide fragments. The peptide sequence and the corresponding oligonucleotides were the following: YQQWQING (Sequence ID No. 6) which is found within Lys-C fragment L7. The corresponding coding and complementary oligonucleotides were also made. The second Lys-C fragment peptide (L1) DIQCCDEK (Sequence ID No. 7) and the corresponding coding and complementary oligonucleotides were also made. In addition, four of the oligonucleotides based on the two Lys-C peptide fragments had sequences corresponding to a Not 1 restriction endonuclease site built at their 5' end.

These peptides were chosen from the eight available peptide sequences because of their low degeneracy. Intial PCR analysis was performed using 10 ng of total library DNA as a substrate. Each arm primer was used with each of the four degenerate primers to generate product. As a control for non-specific product formation every primer was also run alone with the total library DNA as a substrate. Sizes of the PCR products were estimated by comparing migration through a 1.5% agarose gel relative to a φX174 RF DNA/HaeIII marker (BRL).

The product of primer pair λ1, and the complementary oligonucleotide to LysC fragment (L1) (Sequence ID No. 7) was cut with Not 1 and Spe 1, subcloned into a vector containing Not 1 and Spe 1 sites, and sequenced. The sequencing confirmed that this PCR product contained within it both Lys-C fragments used to construct the primers as well as the Lys-C peptide sequences of fragments L4, L5 and L6.

The PCR product of primer pair 1,4 was then used as a hybridization probe to screen the cDNA library directly. This was done to eliminate any possible PCR generated sequence errors, rather than generating the entire cDNA directly using PCR. Screening initially produced numerous positive phage plaques. 20 plaques were isolated and PCR analysis was performed on these 20 positive plaques using primer λ1 and 4, thus amplifying the 5' end of the cDNA. Five of the 20 plaques gave a product of ~500 base pairs, the remainder gave smaller or no bands. Presumably the absence of a band was due to inserts which were oriented in the opposite direction.

Two of the phagemids containing the longest inserts were grown and sequenced. Sequencing revealed an uninterrupted open reading frame of 513 nucleotides which contained all of the Lys-C fragments. It was followed by a 60 nucleotide 3' untranslated region followed by a poly A tract. A hexa nucleotide AATAAA consensus sequence was located 15 nucleotides before the poly (A) + tract. Only 12 nucleotides of 5'-untranslated region were found in any of the sequenced clones. This is possibly due to premature termination of the reverse transcriptase during the construction of the tick library.

Using the computer program SIGSEQ2, which can be used to predict the region of the protein which is the signal peptide, the predicted peptidase cleavage occurs between amino acids 15 and 16(Ser and I1). This cleavage results in a mature protein of 156 amino acids with a predicted molecular weight of 17,256. The predicted moubatin protein sequence was compared with that of other protein sequences in the Swiss PROT data base. No significant homology was found.

Construction of pKH4α2

Construction of pKH4 is described in Schultz, et al., *Gene* 61 (1987) 123–133, which is incorporated by reference. The plasmid pJC197 (Schultz et al. *Gene* 54 (1987) 113–123) is an *E. coli - S. cerevisiae* shuttle vector which contains a unique BamHI cloning site between the yeast MFα1 pre-pro leader and transcriptional terminator, originally described in Kurjan and Herskowitz (1982) ibid. pJC197 was digested with EcoRI+PstI, and the 0.7-kb PstI-EcoRI fragment containing a portion of the MFα1 pre-pro-leader, a three-frame translational terminator, and MFαI transcriptional terminator, was gel-purified. GAL10p was isolated from YEP51 by digestion with Sau3A, flush-ending with PolIk, ligating with octameric BamHI linkers, and digestion with SalI.

The resulting 0.5-kb BamHI-SalI fragment bearing GAL10p was gel purified and ligated to a 35-bp SalI-PstI synthetic oligodeoxynucleotide adapter encoding the first 11 bp of the MFα1 nontranslated leader plus the ATG and first 8 aa of the MFα1 pre-pro-leader. The resulting 0.5-kb fragment was digested with BamHI, gel-purified, and ligated together with the aforementioned 0.7-kb PstI-EcoRI fragment plus the 4.0 kb EcoRI-BamHI vector fragment derived from pBR322. The resulting plasmid, pKH207-1, contains GAL10p fused to the MFα1 pre-pro-leader plus BamHI cloning site, translational termination codons, and MFα1 transcriptional terminator. Upon digestion with EcoRI and partial digestion with BamHI, an expression cassette of GAL10p fused to the yeast MFα1 pre-pro-leader, a unique BamHI cloning site, translational termination codons in all three reading frames, and MFα1 transcriptional terminator sequence was inserted into the yeast shuttle vector pCl/1 (Rosenberg et al. Nature 312 (1984) 77-80) which contains the yeast 2μ DNA sequence for stable propagation of the plasmid in yeast at high copy number, to form pKH4.

A 213-bp BamHI-PstI fragment encoding aa 9-79 of the ppL was prepared from the plasmid pα2 (Bayne et al., Gene 66 (1988) 235-244). The plasmid pα2 contains a portion of the yeast MFα1 pre-pro sequence (79aa) modified at codons 80 and 81 to create a BamHI site 6 aa upstream from the KEX2 processing site. The region corresponding to codon 9 (PstI) of the ppL to the BamHI site of pKH4 was removed from pKH4 after digestion with BamHI followed by partial digestion with PstI. The modified vector, pKH4α2 was prepared by replacement of this excised sequence with the BamHI-PstI fragment from pα2. Plasmid pKH4α2 contains the yeast GAL10 promoter, a portion of the MFα1 pre-pro leader (79 aa), a three-frame translational terminator and MFα1 transcriptional terminator, the yeast LEU2 gene, yeast 2μ sequences, pBR322 derived sequences, including the $Ap^R$ gene and the origin of DNA replication (ori).

Construction of Moubatin Expression Vector

The predicted mature protein coding sequence was expressed in yeast using the expression vector pKH4α2. The coding sequence was isolated by PCR, generating a DNA fragment using the Bluescript SK phagemid vector containing the moubatin cDNAs as a substrate and the oligo primers, Sequence ID Nos. 3 and 4.

FIG. 1 shows construction of the yeast plasmid expression vector used for the expression of the Moubatin gene sequence. Representations are:

Moubatin coding sequence

α-mating factor gene sequences

2μ circle sequences pBR322 sequences $leu2^d$ gene sequences

GAL 10 promoter sequence

Transformation of Saccharomyces cerevisiae BJ1995

The haploid Saccharomyces cerevisiae strain BJ1995 (MAT, $leu^2$, $trp^1$, $prb^{1-1122}$, $pep^{4-3}$ cir+; a gift from Elizabeth Jones, Carnegie-Mellon University) was made cir° by standard techniques and transformed using the procedure of Hinnen et al. (1978) Proc. Natl. Acad. Sci. USA 75: 1929-1933. Transformant clones were selected on leucine-minus agar plates and propagated at 30° C. in 5×Leu- medium, containing 4% glucose. At a cell density of $A_{600}$=6-9, the cells were harvested by centrifugation and resuspended at the same cell density in 5×Leu- medium containing 2% galactose for induction. After 48 hour induction at 30° C., the cells were removed by centrifugation and the medium was evaluated for the expression of moubatin (see below). A clonal isolate for a pre-Master seed was stored at −70° C. in the presence of 17% (v/v) glycerol for all further fermentation and protein purification studies.

Purification of Recombinant Moubatin

Yeast cells were sedimented by centrifugation and the remaining cell free culture medium was diluted

5' ATATGGATCC TGTCTTTGGA TAAAAGAATT GCATATGCTC AAAGCGGA 3'

5' ATATCGGGAT CCTATTTTGC GGAAGTCTCG CA 3'

These primers contain a BamH1 site for subcloning and insert codons for a yeast KEX2 protease cleavage site (Lys-Arg) N-terminal to the predicted signal peptidase cleavage site of the native protein. KEX2 protease cleaves on the carboxy terminal side of Lys-Arg enabling generation of the authentic N-terminus of moubatin which is produced and secreted by the yeast.

The PCR resulted in a blunt end fragment which was digested with BamH1. The correct fragment was obtained after electrophoresis in a 1% agarose gel, excision of the band and electroelution (before ligation the vector was digested with BamH1 and treated with calf intestine alkaline phosphatase). The fragment was purified and then ligated into the yeast expression vector pKH4α2. The sequence and orientation of the final isolated clones was confirmed by DNA sequence analysis.

5-fold with 20 mM NaAcetate buffer, pH 4.0, and applied to a Fast S sepharose column that had been previously equilibrated with the same buffer. The column was washed with 5 column volumes of the same buffer and the recombinant moubatin eluted with a 0-1.0 M NaCl gradient in the same buffer. The fractions were screened for moubatin by assay for platelet aggregation inhibitory activity. The peak fractions were pooled, concentrated in a speed vac, and applied to a reverse phase $C_{18}$ HPLC column. Purified recombinant moubatin was eluted with a linear gradient of 17-50% isopropanol, 0.08% trifluoroacetic acid over 45 min. The fractions were dried in a speed vac and dissolved in 20 mM NaAcetate pH 7.3 and assayed for aggregation inhibitory activity and purity by SDS-PAGE. The final isolated moubatin was quantified by amino acid composition analysis and its identity and purity confirmed by amino terminal amino acid sequence analysis.

Deposit

The transformed yeast strain pKH4α2•Moubatin, deposited with the American Type Culture Collection, Rockville, Md., USA, is designated ATCC 74136. The deposit was made Feb. 24, 1992 under the provisions of the Budapest Treaty on the International Recognition of the Deposit of Microorganisms for the Purposes of Patent Procedure and the Regulations thereunder (Budapest Treaty). Maintenance of a viable culture is assured for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention rights granted under the authority of any government in accordance with its patent laws.

Therapy

The proteinaceous substance of this invention, which blocks stimulation of platelet aggregation by collagen, forms pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminium; and organic primary, secondary and tertiary amines, as for example, trialkylamines, including triethylamine, procaine, dibenzylamine, 1-ethenamine; N,N'-dibenzylethylenediamine, dihydroabietylamine, N-(lower)alkylpiperidine, and any other suitable amine.

The antithrombotic blood concentration of the proteinaceous substance of this invention which blocks stimulation of platelet aggregation by collagen is about 200 nMolar (or 3.2 μg/ml).

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Although the proteinaceous substance of this invention may survive passage through the gut following oral administration, applicants prefer non-oral administration, for example, subcutaneous, intravenous, intramuscular or intraperitoneal; administration by depot injection; or by implant preparation.

For parenteral administration the proteinaceous substance of this invention may be administered as injectable dosages of a solution or suspension of the substance in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The proteinaceous substance of this invention can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

---

What is claimed is:

1. A purified protein having a molecular weight of about 17,000, an amino acid sequence identified as SEQ. ID NO: 2, and a capacity to inhibit collagen-stimulated platelet aggregation wherein the protein is derived from the tick *Ornithodoros moubata*.

2. The product of a process for the production of a protein derived from *Ornithodoros moubata* tick extract and having a molecular weight of about 17,000, an amino acid sequence identified as SEQ. ID NO 2 and a capacity to inhibit collagen-stimulated platelet aggregation, comprising the steps of:
   a) disrupting *Ornithodoros moubata* ticks;
   b) homogenizing and solubilizing tick extract in an aqueous solution comprising a buffered salt having a suitable fixed pH to produce a homogenate;
   c) centrifuging the homogenate to produce supernatant protein suspension fractions; and
   d) assaying the fractions and selecting a product fraction characterized by its inhibition of collagen-stimulated platelet aggregation.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 594 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:1:

```
AAAGCAGTCA   ACATGATGCT   GGTTTTGACG   ACCCTGATTT   TCTCCTTTTC   TGCGAGCATT        6 0

GCATATGCTC   AAAGCGGATG   CTCTGTAAGC   GACCCTCTCG   ACGCCTTGAA   AGCTTTCAAG        1 2 0
```

|  |  |  |  |  |  |
|---|---|---|---|---|---|
| GACGGTGCAG | GAACATTCCT | TCTACAGAAA | TCCACAGATC | CCCAAGCAAG | GGACTGCTTG | 180 |
| AAAGGGACCC | CGAATGGAAA | TAGAGACGGC | AACACGTTGC | CAGTGACAAT | GACGTACAAG | 240 |
| GACGACTCCA | AGTGGGTTTC | ATTGAATTGG | ATGTTTACTT | TGGAAGGCGC | AAATATAGTC | 300 |
| GCAACCTTAG | AAGGAAAGCG | AAAGCAACGG | GGGGAACTAG | TCTACGACGT | GCAAAGTCAT | 360 |
| GACTGCCATA | TTACCAAGCT | CTCCTCGGGC | GTGTATCAGC | AGTGGCAGAG | CAATGGCTCA | 420 |
| GCAGATGACA | AGGACATTAA | GTGCTGCGAT | GAGAAATTTA | AGGAGTTGAC | GTCTGGTATT | 480 |
| GACTACACAA | AGCCCCAAGA | GAAGGGCTGC | GAGACTTCCG | CAAAATGAAG | AACCTACAGG | 540 |
| CATCTCATCA | CACTGAAAGA | ATTCCAATAA | ACTGCTTTAT | AAACAAAAAA | AAAA | 594 |

( 2 ) INFORMATION FOR SEQ ID NO:2:

( i ) SEQUENCE CHARACTERISTICS:
        ( A ) LENGTH: 171 amino acids
        ( B ) TYPE: amino acid
        ( C ) STRANDEDNESS: unknown
        ( D ) TOPOLOGY: unknown     ( i i ) MOLECULE TYPE: peptide     ( x i ) SEQUENCE DESCRIPTION: SEQ ID NO:2:

```
Met Met Leu Val Leu Thr Thr Leu Ile Phe Ser Phe Ser Ala Ser Ile
 1               5                  10                  15

Ala Tyr Ala Gln Ser Gly Cys Ser Val Ser Asp Pro Leu Asp Ala Leu
            20                  25                  30

Lys Ala Phe Lys Asp Gly Ala Gly Thr Phe Leu Leu Gln Lys Ser Thr
        35                  40                  45

Asp Pro Gln Ala Arg Asp Cys Leu Lys Gly Thr Pro Asn Gly Asn Arg
    50                  55                  60

Asp Gly Asn Thr Leu Pro Val Thr Met Thr Tyr Lys Asp Asp Ser Lys
65                  70                  75                  80

Trp Val Ser Leu Asn Trp Met Phe Thr Leu Glu Gly Ala Asn Ile Val
                85                  90                  95

Ala Thr Leu Glu Gly Lys Arg Lys Gln Arg Gly Glu Leu Val Tyr Asp
            100                 105                 110

Val Gln Ser His Asp Cys His Ile Thr Lys Leu Ser Ser Gly Val Tyr
        115                 120                 125

Gln Gln Trp Gln Ser Asn Gly Ser Ala Asp Asp Lys Asp Ile Lys Cys
    130                 135                 140

Cys Asp Glu Lys Phe Lys Glu Leu Thr Ser Gly Ile Asp Tyr Thr Lys
145                 150                 155                 160

Pro Gln Glu Lys Gly Cys Glu Thr Ser Ala Lys
                165                 170
```

( 2 ) INFORMATION FOR SEQ ID NO:3:

( i ) SEQUENCE CHARACTERISTICS:
        ( A ) LENGTH: 48 base pairs
        ( B ) TYPE: nucleic acid
        ( C ) STRANDEDNESS: unknown
        ( D ) TOPOLOGY: unknown     ( i i ) MOLECULE TYPE: peptide     ( x i ) SEQUENCE DESCRIPTION: SEQ ID NO:3:

ATATGGATCC TGTCTTTGGA TAAAAGAATT GCATATGCTC AAAGCGGA        48

( 2 ) INFORMATION FOR SEQ ID NO:4:

( i ) SEQUENCE CHARACTERISTICS:
        ( A ) LENGTH: 32 base pairs (B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:4:

ATATCGGGAT CCTATTTTGC GGAAGTCTCG CA                                32

(2) INFORMATION FOR SEQ ID NO:5:

(i) SEQUENCE CHARACTERISTICS:
    (A) LENGTH: 20 base pairs
    (B) TYPE: nucleic acid
    (C) STRANDEDNESS: unknown
    (D) TOPOLOGY: unknown (ii) MOLECULE TYPE: DNA (genomic)

(xi) SEQUENCE DESCRIPTION: SEQ ID NO:5:

GCTCTAGAAC TAGTGGATCC                                              20

(2) INFORMATION FOR SEQ ID NO:6:

(i) SEQUENCE CHARACTERISTICS:
    (A) LENGTH: 8 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:6:

Tyr Gln Gln Trp Gln Ile Asn Gly
    1               5

(2) INFORMATION FOR SEQ ID NO:7:

(i) SEQUENCE CHARACTERISTICS:
    (A) LENGTH: 8 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:7:

Asp Ile Gln Cys Cys Asp Glu Lys
    1               5